US009863926B2

(12) United States Patent
Kriel et al.

(10) Patent No.: US 9,863,926 B2
(45) Date of Patent: Jan. 9, 2018

(54) CONDENSATE-GAS RATIOS OF HYDROCARBON-CONTAINING FLUIDS

(71) Applicant: SGS North America Inc., Rutherford, NJ (US)

(72) Inventors: Wayne A. Kriel, Friendswood, TX (US); Jerry W. Swearingen, Jr., Cypress, TX (US)

(73) Assignee: SGS North America Inc., Rutherford, NJ (US)

( * ) Notice: Subject to any disclaimer, the term of this patent is extended or adjusted under 35 U.S.C. 154(b) by 511 days.

(21) Appl. No.: 14/258,976

(22) Filed: Apr. 22, 2014

(65) Prior Publication Data
US 2015/0300997 A1    Oct. 22, 2015

(51) Int. Cl.
| | |
|---|---|
| *G01N 33/28* | (2006.01) |
| *G01N 1/22* | (2006.01) |
| *G01N 30/02* | (2006.01) |
| *G01N 30/32* | (2006.01) |
| *G01N 7/00* | (2006.01) |

(52) U.S. Cl.
CPC ....... *G01N 33/2823* (2013.01); *G01N 1/2211* (2013.01); *G01N 7/00* (2013.01); *G01N 2030/025* (2013.01); *G01N 2030/324* (2013.01)

(58) Field of Classification Search
CPC .... G01N 33/2823; G01N 1/2211; G01N 7/00; G01N 2030/324; G01N 2030/025
See application file for complete search history.

(56) References Cited

U.S. PATENT DOCUMENTS

| | | | | |
|---|---|---|---|---|
| 3,257,609 | A * | 6/1966 | Sanford | G01N 27/423 204/409 |
| 3,367,850 | A * | 2/1968 | Johnson | G01N 33/2847 204/430 |
| 4,621,518 | A * | 11/1986 | Gerdes | G01N 30/00 73/23.35 |
| 4,737,271 | A * | 4/1988 | Childs | B04C 5/13 209/2 |
| 4,849,107 | A * | 7/1989 | Thew | B04C 5/081 209/727 |
| 6,245,955 | B1* | 6/2001 | Smith | C10L 3/00 585/15 |
| 6,401,529 | B1 | 6/2002 | Robison et al. | |
| 7,147,788 | B2* | 12/2006 | Tveiten | B01D 17/00 209/12.1 |
| 7,942,065 | B2* | 5/2011 | Xie | G01F 15/02 73/861.04 |
| 8,109,334 | B2* | 2/2012 | Goodwin | E21B 49/10 166/250.01 |

(Continued)

FOREIGN PATENT DOCUMENTS

EP            24148 A1    2/1981

OTHER PUBLICATIONS

Kriel et al., "Improved Gas Chromatographic Analysis of Reservoir Gas and Condensate Samples," SPE International Symposium on Oilfield Chemistry, Mar. 1, 1989, pp. 397-411.

(Continued)

*Primary Examiner* — John Fitzgerald
(74) *Attorney, Agent, or Firm* — Fish & Richardson P.C.

(57) ABSTRACT

Analyzing a hydrocarbon-containing fluid includes providing a hydrocarbon-containing fluid to a separation system including a cyclone separator, and separating the hydrocarbon-containing fluid into a gas phase sample and a liquid phase sample. The liquid phase sample is separated into an aqueous sample and a non-aqueous sample. The volume of the gas phase sample and of the non-aqueous sample are assessed, and the ratio of the volume of the non-aqueous sample to the volume of the gas phase sample yields the condensate-gas ratio.

22 Claims, 3 Drawing Sheets

(56) References Cited

U.S. PATENT DOCUMENTS

| | | | |
|---|---|---|---|
| 8,857,519 B2 * | 10/2014 | Hale | E21B 43/017 166/267 |
| 2003/0168391 A1 | 9/2003 | Tveiten | |
| 2009/0139345 A1 * | 6/2009 | Xie | G01F 15/02 73/861.04 |
| 2010/0269696 A1 * | 10/2010 | Sarshar | B01D 17/0217 95/243 |
| 2011/0005745 A1 * | 1/2011 | Goodwin | E21B 49/10 166/250.01 |
| 2012/0155964 A1 * | 6/2012 | Carter | E21B 43/0122 405/60 |
| 2013/0043035 A1 * | 2/2013 | Hale | E21B 43/017 166/338 |

OTHER PUBLICATIONS

Rodger, "Multiphase Flow Measurement in the Gas Industry," Proceedings of the 2002 American School of Gas Measurement Technology, Jan. 12, 2002, pp. 241-246.

Couteau, International Search Report and Written Opinion for International patent application No. PCT/US2015/026838, dated Jul. 14, 2015, 14 pages.

Wang et al., "The State-of-the-Art of Gas-Liquid Cylindrical Cyclone Control Technology: From Laboratory to Field," Journal of Energy Resources Technology, vol. 132, Sep. 2010, 9 pages.

Gomez et al., "Aspect Ratio Modeling and Design Procedure for GLCC Compact Separators," Journal of Energy Resource Technology, vol. 121(1), Mar. 1999, pp. 15-23.

Shoham et al., "State of the Art of Gas/Liquid Cylindrical-Cyclone Compact-Separator Technology," Distinguished Author Series, Society of Petroleum Engineers, SPE 39600, Jul. 1998, pp. 58-65.

Wang et al., "Gas-Liquid Cylindrical Cyclone (GLCC© ) Compact Separators for Wet Gas Applications," Journal of Energy Resources Technology, vol. 125, Mar. 2003, pp. 43-50.

Wang et al., "Gas-Liquid Cylindrical Cyclone (GLCC© ) Compact Seperators for Wet Gas Applications," Proceeding of ETCE 2001, Engineering Technology Conference on Energy, Feb. 5-7, 2001, 11 pages.

* cited by examiner

CONDENSATE-GAS RATIOS OF HYDROCARBON-CONTAINING FLUIDS

BACKGROUND

The present disclosure relates to systems and methods for analyzing hydrocarbon-containing fluids by cyclonic separation.

In oil and gas production, hydrocarbon-containing fluids are analyzed for allocation purposes, by determining gas-to-oil ratios, fluid shrinkage, and gas composition. Gas-liquid separators have been utilized for fluid separation and analysis during the testing and production phases of hydrocarbon bearing operations. Current separation methods include gravity separation in large vessels and centrifugal separation. Many of these methods, however, involve equipment that is large, bulky, and difficult to transport.

SUMMARY

In a first general aspect, analyzing a hydrocarbon-containing fluid includes providing a hydrocarbon-containing fluid to a cyclone separator, separating the hydrocarbon-containing fluid into a gas phase sample and a liquid phase sample via the cyclone separator, and separating the liquid phase sample into an aqueous sample and a non-aqueous sample. Analyzing the hydrocarbon-containing fluid further includes assessing the volume of the gas phase sample, assessing the volume of the non-aqueous sample, and assessing the condensate-gas ratio of the hydrocarbon-containing fluid, where the condensate-gas ratio of the hydrocarbon-containing fluid is the ratio of the volume of the non-aqueous sample to the volume of the gas phase sample.

Implementations of the first general aspect may include one more of the following features.

In some cases, assessing the volume of the non-aqueous sample includes locating an interface between the aqueous sample and the non-aqueous sample. The non-aqueous sample may be collected in a container after assessing the volume of the non-aqueous sample. The composition of the gas phase sample may be assessed. Assessing the composition of the gas phase sample may include providing a portion of the gas phase sample to a gas chromatograph. Fixed gases and C1-C5 compounds in the gas phase sample may be assessed with the gas chromatograph. An aggregate of hexanes and C6+ compounds in the gas phase sample may be identified. Assessing the volume of the gas phase sample may include adjusting the volume of the gas phase sample based on the composition of the gas. In some cases, the moisture content of the gas phase sample, the temperature of the gas phase sample, or both may be assessed. In certain cases, the hydrocarbon-containing fluid is directed from a hydrocarbon production line to an inlet of the cyclone separator.

In a second general aspect, an apparatus for analyzing a hydrocarbon-containing fluid includes a cyclone separator adapted to separate a hydrocarbon-containing fluid into a gas phase sample and a liquid phase sample, a flow meter adapted to assess a volume of the gas phase sample from the cyclone separator, and a receptacle adapted to receive the liquid phase sample from the cyclone separator. The liquid phase sample includes an aqueous sample and a non-aqueous sample. A controller is operably coupled to the flow meter and the receptacle. The controller is configured to assess a condensate-gas ratio of the hydrocarbon-containing fluid (i.e., the ratio of the volume of the non-aqueous sample to the volume of the gas phase sample).

Implementations of the second general aspect may include one or more of the following features.

In some cases, cyclone separator defines a cyclone chamber having a longitudinal axis, and a length of the cyclone separator along the longitudinal axis is up to two meters. The cyclone chamber may define a fluid inlet, a gas outlet, and a liquid outlet. In one example, a diameter of the liquid outlet is in a range between 1 cm and 5 cm. The cyclone chamber may further include a first chamber defining the gas outlet, a second chamber defining the liquid outlet, and a third chamber between the first chamber and the second chamber defining the fluid inlet. The first chamber, the second chamber, and the third chamber are typically fluidly coupled and aligned along the longitudinal axis. An inner diameter of the second chamber may decrease linearly from the diameter of the third chamber to the diameter of the liquid outlet. The third chamber generally includes one or more trap regions, each trap region fluidly coupled to the receptacle via a conduit. The apparatus may include a gas chromatograph adapted to receive a portion of the gas phase sample. In some cases, a user interface is communicably coupled to the controller. In certain cases, a moisture sensor and a temperature sensor are communicably coupled to the controller and configured to assess the moisture and the temperature, respectively, of the gas phase sample. The receptacle may include a sight glass, and the analysis system may include a camera adapted to record the location of an interface between the aqueous sample and the non-aqueous sample in the sight glass.

The methods and apparatus described herein provide advantages including improved portability and mobility. The analysis system is compact, which is particularly advantageous in locations such as offshore well structures where operating space is limited, remote, and/or hard to access. Other advantages include near real time data collection and reporting, collection of pressurized liquid samples, determination of liquid yields on ultra-lean gas systems, monthly allocation work, and exploration of condensate producing wells.

These general and specific aspects may be implemented using a device, system or method, or any combination of devices, systems, or methods. The details of one or more embodiments are set forth in the accompanying drawings and the description below. Other features, objects, and advantages will be apparent from the description and drawings, and from the claims.

DETAILED DESCRIPTION

The present disclosure relates to assessing the condensate-gas ratio of a hydrocarbon-containing fluid by cyclonic separation. In one example, such as a reservoir fluid, the hydrocarbon-containing fluid is unrefined. In another example, such as a hydrocarbon-containing fluid in a pipeline, the hydrocarbon-containing fluid is at least partially refined. The condensate-gas ratio is assessed by separating the hydrocarbon-containing fluid into a gas phase sample and liquid phase sample, assessing the volume of the gas phase sample and the non-aqueous portion of the liquid phase sample (the "condensate"), and calculating the ratio of the volume of the non-aqueous portion of the liquid phase sample to the volume of the gas phase sample.

As described herein, cyclonic separation is used to separate a hydrocarbon-containing fluid into a gas phase sample and a liquid phase sample. Separation is accomplished in an apparatus generally referred to as a cyclone separator. The hydrocarbon-containing fluid is typically provided to the cyclone separator as a stream (e.g., a continuous stream) from a source, such as a pipeline or other conduit, used for transporting the hydrocarbon-containing fluid. In some cases, the hydrocarbon-containing fluid is provided to the cyclone separator from a fixed-volume container (e.g., a sample cylinder). The hydrocarbon-containing fluid is provided to the cyclone separator in such a way as to establish high speed rotation of the sample in a helical pattern within an interior chamber of the cyclone separator. The angle at which the fluid is provided to the interior chamber, the geometry of the interior chamber, and the flow rate of the fluid can be selected such that the hydrocarbon-containing fluid is separated into a gas phase sample and a liquid phase sample, with the gas phase sample migrating toward an upper end of the cyclone separator, and the liquid phase sample draining toward a lower end of the cyclone separator. Thus, the separation process itself is achieved in the absence of filters and in the absence of supplied electrical power.

Figure 1:
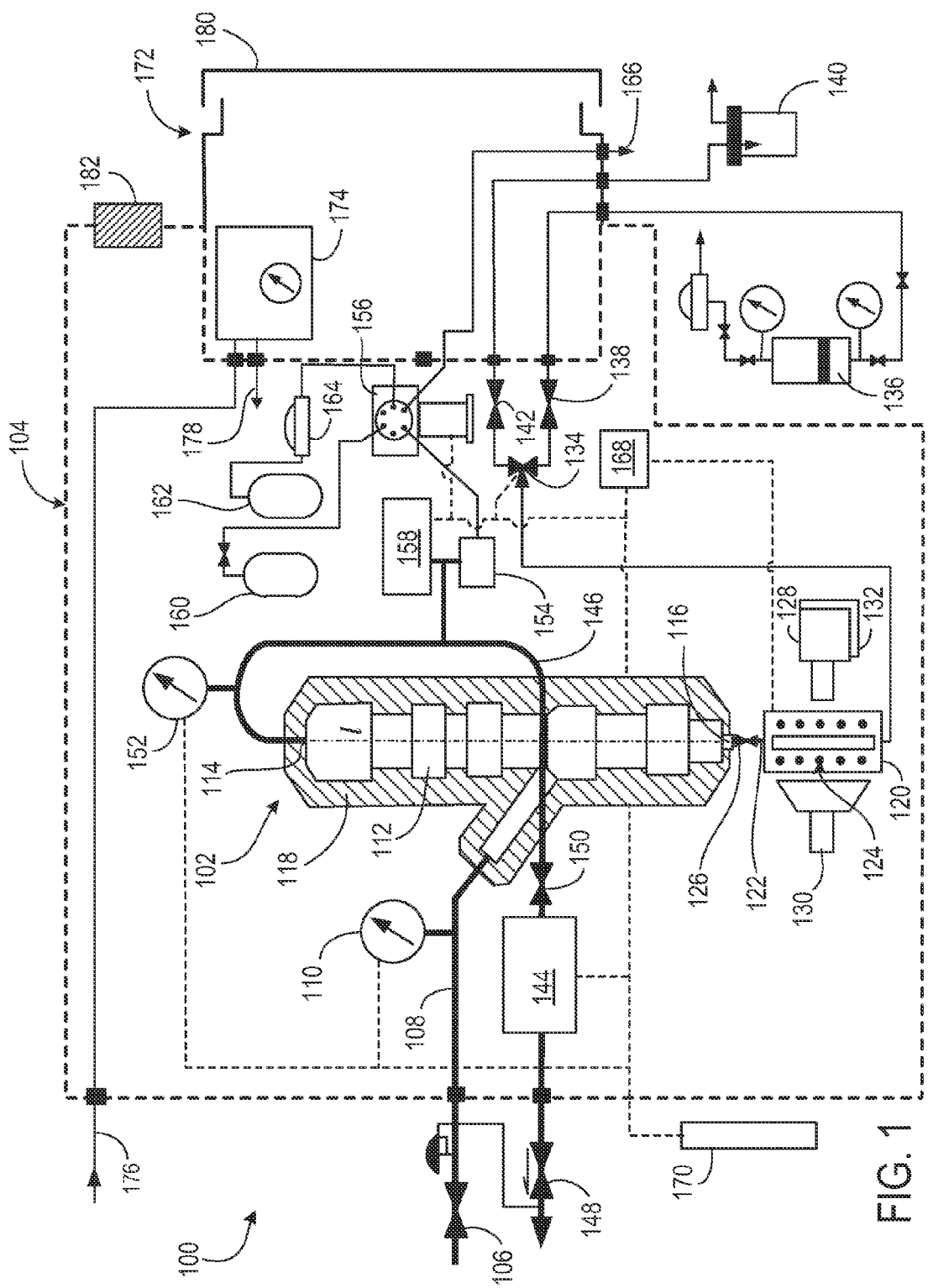
FIG. 1 depicts an analysis system.

FIG. 1 depicts an analysis system 100 for assessing the condensate-gas ratio for a hydrocarbon-containing fluid via cyclonic separation. Analysis system 100 includes a cyclone separator 102 enclosed in housing 104. An inlet 106, configured to receive a hydrocarbon-containing fluid, is coupled to the cyclone separator 102 via a conduit 108. In some cases, a pressure sensor 110 is coupled to the conduit 108. The cyclone separator 102 is generally cylindrical in shape and defines an interior chamber 112. A longitudinal axis l runs along the length of the cyclone separator 102, from a first end 114 to a second end 116. After separation of the hydrocarbon-containing fluid into a gas phase sample and a liquid phase sample in the cyclone separator 102, the gas phase sample exits the cyclone separator via first end 114, and the liquid phase sample exits the cyclone separator via the second end 116. In some cases, the cyclone separator 102 is at least partially covered with a jacket 118. The jacket 118 may heat the cyclone separator 102, insulate the cyclone separator, or both.

A receptacle 120 for collecting the liquid phase sample from the cyclone separator 102 is coupled to the second end 116 of the cyclone separator via a conduit 122. Receptacle 120 may include sight glass 124, through which the contents of the receptacle 120, including an interface between an aqueous sample and a non-aqueous sample of the liquid phase sample, can be viewed. In some cases, the conduit 122 includes a drain valve 126. The analysis system 100 includes a camera 128 adjacent the receptacle 120, and a back light 130 opposite the camera. Camera 128 may be a charge-coupled device, a digital camera, a video camera, or the like. In some cases, the camera 128 is mounted to translation device(s) 132 to allow translation in one or more directions relative to the receptacle 120. In one example, the translation device 132 includes a syringe pump operably connected to the camera 128 and configured to translate the camera along the height of the receptacle 120. Translation device(s) 132 may also be configured to allow translation of camera 128 along the width or length of the receptacle 120. The receptacle 120 allows visual identification of volume, for example, through markings on the side of the receptacle. The liquid phase sample collected in receptacle 120 passes through a two-way selector valve 134, which allows separation of the liquid stream into a non-aqueous sample and an aqueous sample. The non-aqueous sample is provided to vessel 136 via metering valve 138, and the aqueous sample is provided to vessel 140 via metering valve 142.

A flow meter 144 is coupled to the first end 114 of the cyclone separator 102 via a conduit 146. Gas flowing through the flow meter 144 exits the analysis system 100 via outlet 148. In some cases, a regulator valve 150 controls the flow rate of the gas phase sample in the conduit 146 to flow meter 144. A pressure sensor 152 is typically coupled to the conduit 146. The conduit 146 is coupled to back pressure regulator 154, leading to gas chromatograph 156. Sensor 158, which may be a moisture sensor, a temperature sensor, or both, separately or together, is coupled to the conduit 146 between the cyclone separator 102 and the regulator valve 150. A calibration gas source 160 and a carrier gas source 162 are coupled to gas chromatograph 156. Carrier gas from carrier gas source 162 is provided to gas chromatograph 156 via regulator 164 adapted to attenuate pressure from the carrier gas source to the gas chromatograph. The gas chromatograph 156 is coupled to the atmosphere via vent 166.

The gas chromatograph 156 identifies and quantifies methane (C1) through pentane (C5) compounds, fixed gases, and an aggregate of hexanes plus C6+ compounds in the gas phase sample based on elution of peaks compared to a standard. As used herein, "fixed gases" generally refers to one or more non-hydrocarbon gases such as He, $H_2$, $N_2$, $O_2$, $CO_2$. In some cases, only certain fixed gases, such as $N_2$, $O_2$, and $CO_2$, may be identified. In one example, gas chromatograph 156 is a Totalflow Model 8206, available from ABB (Zurich, Switzerland).

The controller 168 is configured to assess a condensate-gas ratio of the hydrocarbon-containing fluid provided to the cyclone separator 102. The controller is operably coupled to the flow meter 144, the drain valve 126, the two-way selector valve 134, and sensors 110, 152, and 158. In some instances, the controller 168 is connected to the jacket 118 (e.g., to control heating or cooling of the cyclone separator 102 via the jacket). The controller 168 is also coupled to a user interface or computing device 170 to enable viewing, analysis, and manipulation of the data output from the analysis system 100. In certain cases, user interface or computing device 170 is linked to a network that allows remote computing devices to communicate with and/or remotely operate the analysis system 100. The user interface or computing device 170 is also coupled to the camera 128, translation device(s) 132, and gas chromatograph 156. In some cases, the user interface or computing device 170 is coupled to a USB port accessible from an exterior of the housing 104 via enclosure 172.

Housing 104 typically has rectangular dimensions in a range of 72 in×28 in×18 in (180 cm×75 cm×50 cm) to 84 in×40 in×30 in (215 cm×100 cm×75 cm). The compact size of the analysis system is advantageous in locations where space is limited, such as offshore well structures. Analysis system 100 typically includes a separate enclosure 172 coupled to but isolated from the atmosphere inside housing 104. Purge gas is provided to regulator 174 via conduit 176, and flows into housing 104 via conduit 178 to establish and maintain a positive pressure in the housing, such that the atmosphere in the housing does not permeate the enclosure and such that potentially explosive atmosphere in the ambient air is inhibited from entering the housing. Regulator 174 and other components, such as the USB port and control switches for two-way selector valve 134, metering valves 138 and 142, and flow regulator valve 150 are accessible via door 180, thereby allowing access to these components while maintaining a positive pressure inside housing 104. In some instances, analysis system 100 includes a purge indicator 182 that provides an indication (e.g., activates a light) when there is positive pressure is in the housing 104.

Figure 2:
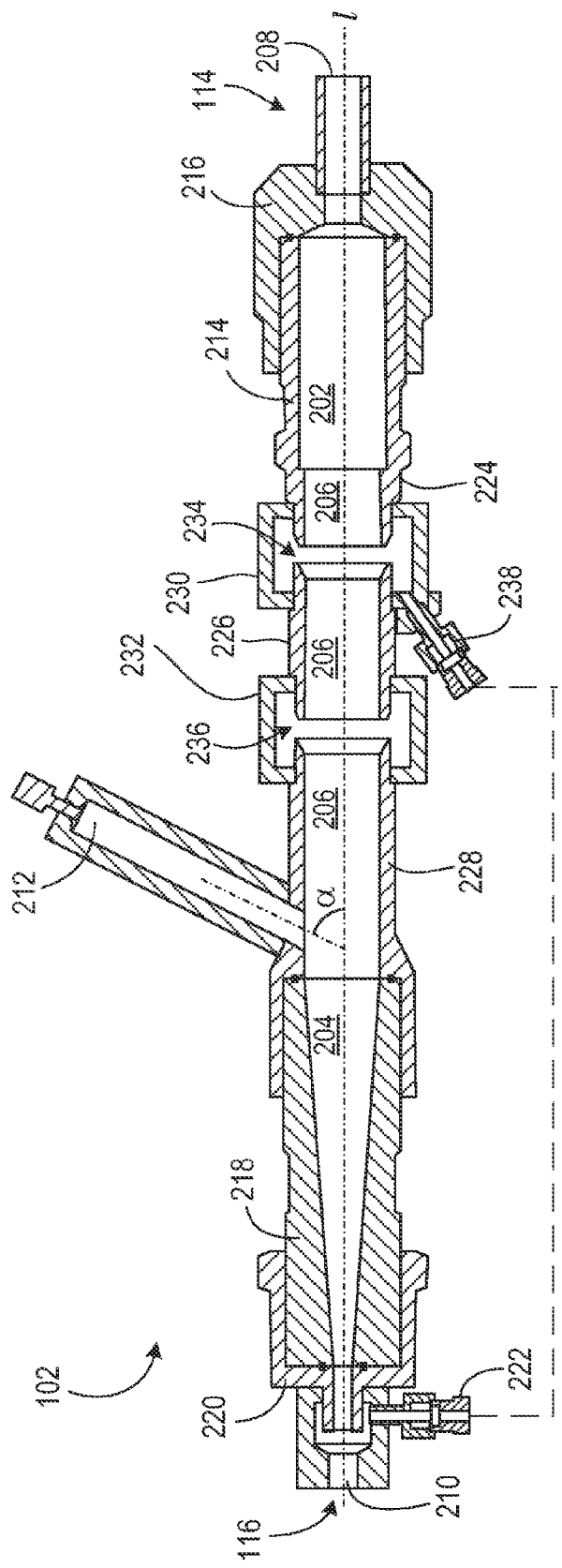
FIG. 2 depicts a cross-sectional view of a cyclone separator.

FIG. 2 depicts a cross-sectional view of an example cyclone separator 102. The length of the cyclone separator 102 along longitudinal axis 1 is typically less than 10 ft (2 m). In one example, the length of the cyclone separator 102 is between 1.5 ft (0.5 m) and 5 ft (1.5 m). The cyclone separator 102 is typically made of stainless steel, but can include other materials such as treated aluminum.

The cyclone separator 102 includes a first chamber 202 at first end 114, a second chamber 204 at second end 116, and a third chamber 206 positioned between the first chamber and the second chamber. First chamber 202 is coupled to a gas outlet 208, and second chamber is coupled to a liquid outlet 210. Third chamber 206 is coupled to a fluid inlet 212. The first chamber 202, the second chamber 204, and the third chamber 206 form an interior chamber aligned along the longitudinal axis 1.

The first chamber 202 is defined by cylindrical section 214 and has a circular interior cross-section extending proximate the first end 114 of the cyclone separator 102 to the third chamber 206. The interior diameter of the circular interior cross section is typically in a range between 0.5 in (1 cm) and 6 in (15 cm). End section 216 couples cylindrical section 214 with gas outlet 208. A length of the first chamber 202 is typically in a range between 3 in (7 cm) and 12 in (30 cm).

The second chamber 204 is defined by cylindrical section 218 and has a circular interior cross-section extending from the third chamber 206 toward the second end 116 of the cyclone separator 102. The diameter of the circular interior cross-section decreases from the end adjacent the third chamber 206 toward the second end 116 of the cyclone separator 102. End section 220 couples cylindrical section 218 to liquid outlet 210. In certain instances, fitting 222 extends from the end section 220. A length of the second chamber is typically in a range between 5 in (12 cm) and 12 in (30 cm).

The third chamber 206 is defined by first section 224, second section 226, and third section 228, and extends between the first chamber 202 and the second chamber 204. The first section 224 and the second section 226 are coupled by coupler 230, and the second section 226 and the third section 228 are coupled by coupler 232. The first section 224, second section 226, and third section 228 typically have cylindrical inner walls of the same inner diameter. The inner diameter of the third chamber 206 is typically in a range between 0.5 in (1 cm) and 6 in (15 cm). A length of the third chamber 206 is typically in a range between 8 in (20 cm) and 20 in (50 cm).

The coupler 230 creates a trap region 234 between the first section 224 and the second section 226, and the coupler 232 creates a trap region 236 between the second section 226 and the third section 228. Each of trap regions 234 and 236 has an interior diameter that exceeds the interior diameter of the sections to which it is coupled. Fitting 238 extends from coupler 230. Fitting 238 is typically coupled to fitting 222 in the second chamber 204 via a conduit, such that liquid in the trap region 234 drains to the liquid outlet 210. A similar fitting may extend from coupler 232 and couple to fitting 222, such that liquid in trap region 236 drains to the liquid outlet 210.

The third section 228 is coupled to fluid inlet 212. Fluid inlet 212 is arranged at an angle α with respect to longitudinal axis 1. Angle α is typically in a range between 60° and 65°. The placement and angle of the fluid inlet 212 with respect to the third section 228, as well as the velocity with which the hydrocarbon-containing fluid enters the cyclone separator 102, influence the initial path of the fluid flow in the cyclone separator and effect separation.

Referring to FIGS. 1 and 2, analysis system 100 can be used to provide the condensate-gas ratio for a hydrocarbon-containing fluid provided to the analysis system. First, a hydrocarbon-containing fluid is provided to inlet 106. In one example, a hydrocarbon-containing fluid flows from a production well system to analysis system 100 via inlet 106. The hydrocarbon-containing fluid may be allowed to flow through inlet 106 for a predetermined sampling time. The flow rate of the hydrocarbon-containing fluid may be in a range of 1 actual $ft^3$/min (0.03 $m^3$/min) and 100 $ft^3$/min (3 $m^3$/min), for example, between 4 actual $ft^3$/min (0.1 $m^3$/min) and 60 actual $ft^3$/min (2 $m^3$/min). From inlet 106, the hydrocarbon-containing fluid flows into third chamber 206 of cyclone separator 102. The hydrocarbon-containing fluid is typically provided to the third chamber 206 at a velocity in a range between 10 ft/s (3 m/s) and 40 ft/s (12 m/s). The fluid inlet 212 directs the hydrocarbon-containing fluid into the third chamber 206 at an angle that is generally parallel to a tangent of an interior wall of the third chamber. The fluid in the cyclone separator 102 circles the interior of the separator 102, forcing the liquid phase against the inner sidewalls and the gas phase away from the inner sidewalls. The liquid phase sample generally moves toward the outlet 210, and the gas phase sample generally moves toward the outlet 208. Trap regions 234 and 236 inhibit portions of the liquid phase sample from reaching the first chamber 202.

The liquid phase sample travels through outlet 210 of the cyclone separator 102 and into the receptacle 120 via the conduit 122. The gas phase sample travels through outlet 208 of the cyclone separator 102 through gas conduit 146 to the gas chromatograph 156 through the back pressure regulator 154. The portion of the gas phase sample that enters the gas chromatograph 156 is typically small relative to the total gas phase sample that flows through conduit 146. The back pressure regulator 154 typically alters the pressure of the portion of the gas phase sample that enters the gas chromatograph 156 based on pressure requirements of the gas chromatograph. The temperature and moisture of the gas phase sample is assessed by sensor 158. The portion of the gas phase sample that is not provided to the gas chromatograph 156 exits the analysis system via regulator valve 150 through flow meter 144, which assesses the volume of the gas phase sample not provided to the gas chromatograph 156.

The gas chromatograph 156 identifies components in the gas phase sample based on retention time correlation with known standards. Accordingly, the composition of the gas phase sample is assessed, including relative amounts of fixed (or non-hydrocarbon) gas, the concentration (or mol %) of C1-C5 gases, and the aggregate concentration (or mol %) of C6+ gases. The volume of the gas phase sample as assessed by flow meter 144 is adjusted to correct for the difference between the flow meter calibration gas and the gas phase sample composition as determined by the gas chromatograph. This adjustment can include, for example, multiplying the assessed volume of the gas phase sample by the ratio of the density of the gas phase sample as determined by composition data from the gas chromatograph to the density of the flow meter calibration gas. The adjusted volume of the total gas phase sample may be further adjusted to correspond to the volume at a standard ambient temperature and pressure (i.e., 60° F. (15.5° C.) and an absolute pressure of 14.696 psi (101.325 kPa)). The volume of the portion of the gas phase sample provided to the gas chromatograph 156 is typically negligible compared to the assessed volume. In some cases, data from the flow meter 144 and gas chromatograph 156 are provided to the user interface or computing device 170 via the controller 168 for calculation of the adjusted volume of the gas phase sample.

The liquid phase sample is collected in receptacle 120. The interface between the aqueous sample and the non-aqueous sample is typically visible through the sight glass 124 in receptacle 120. In some instances, the back light 130 allows the receptacle 120 and/or the camera 128 to more easily identify the interface between the aqueous sample and the non-aqueous sample. With selector valve 134 closed, the camera 128 records the location of the interface with respect to indicia in the sight glass 124, as well as the total volume of the liquid in the receptacle 120. The volume of the non-aqueous sample is assessed by calculating the difference between the total volume and the volume associated with the position of the interface between the aqueous sample and the non-aqueous sample.

Selector valve 134 is operated such that the aqueous sample is collected in vessel 140, and the non-aqueous sample is collected in vessel 136. The volume of the liquid phase is entered into the user interface or computing device by an operator viewing the indicia and the sight glass 124 via the camera 128. In some instances, the volume of the non-aqueous sample may be provided to the user interface or computing device 170 automatically (e.g., based on the position of the translation device 132) via controller 168. After the volume of the gas phase sample has been adjusted for composition and converted to standard conditions, the condensate-gas ratio of the hydrocarbon-containing fluid is calculated by dividing the volume of the non-aqueous sample by the adjusted volume of the gas phase sample.

Figure 3:
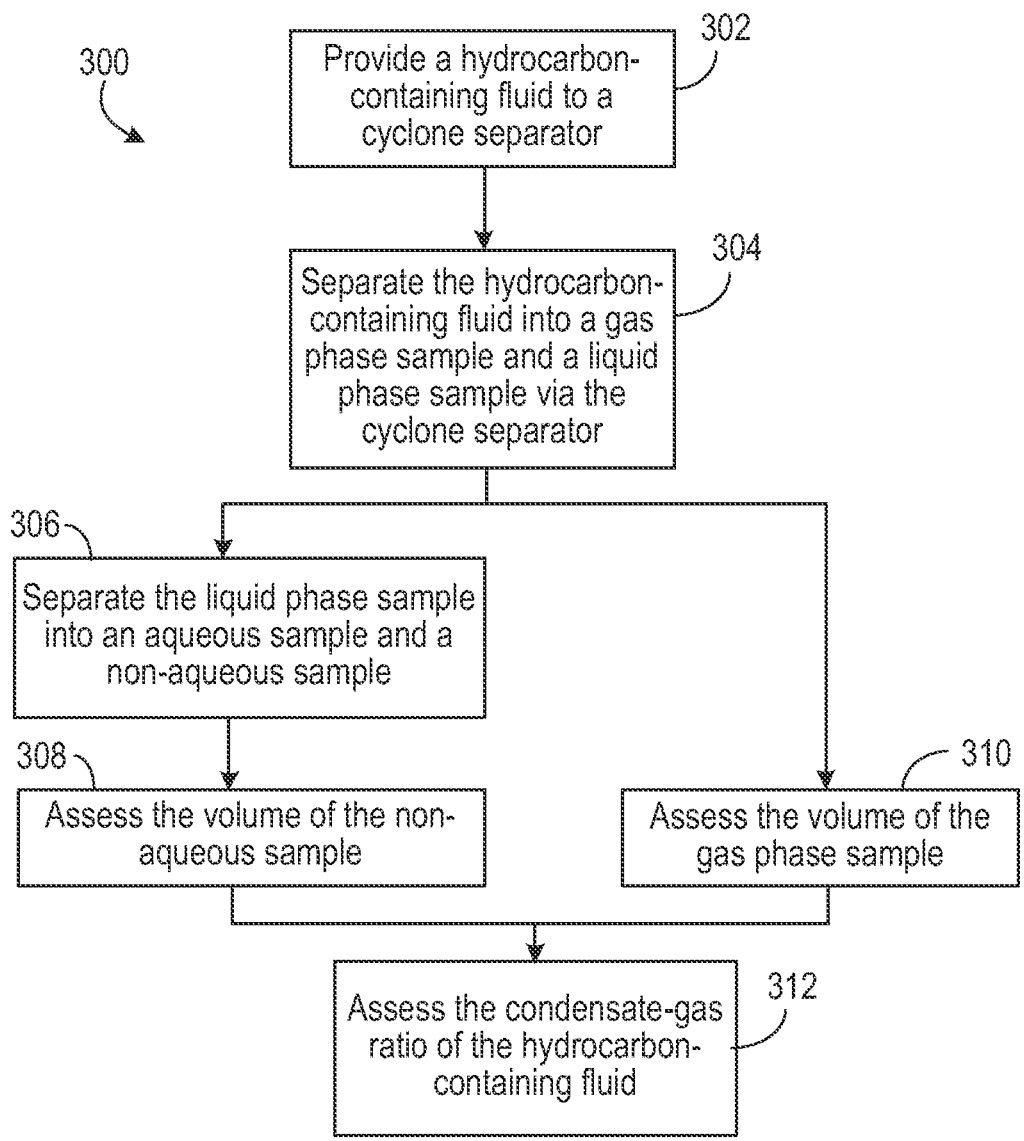
FIG. 3 is a flow diagram of a method for analyzing a hydrocarbon-containing fluid.

FIG. 3 is a flow chart describing a method 300 for assessing a condensate-gas ratio for a hydrocarbon-containing fluid. In 302, a hydrocarbon-containing fluid is continuously provided to a cyclone separator for a given sampling time. For example, referring to FIGS. 1 and 2, a hydrocarbon-containing fluid can be directed from a hydrocarbon production line to the fluid inlet 212 of the cyclone separator 102.

In 304, the hydrocarbon-containing fluid is separated into a gas phase sample and a liquid phase sample. For example, the liquid phase sample travels through outlet 210 of the cyclone separator 102 and into the receptacle 120 via the conduit 122. The gas phase sample travels through outlet 208 of the cyclone separator 102 through conduit 146 to the flow meter 144. In some instances, a regulator valve 150 controls the flow rate of the gas phase sample in the conduit 146 that enters the flow meter 144.

In 306, the liquid phase sample is separated into an aqueous sample and a non-aqueous sample. For example, the fluid level in receptacle 120 may be maintained such that an interface between the aqueous sample and the non-aqueous sample is visible in the sight glass 124.

In 308, the volume of the non-aqueous sample is assessed. The camera 128 may be used to locate the interface between the aqueous sample and the non-aqueous sample in order to assess the volume of the non-aqueous sample. In some instances, the back light 130 allows the receptacle 120 and/or the camera 128 to more easily identify the interface between the aqueous sample and the non-aqueous sample. The assessed volume of the non-aqueous sample is sent to the user interface or computing device 170, for example, via operator input or via controller 168.

A portion of the gas phase sample travels to the gas chromatograph 156 via the back pressure regulator 154. The sensor 158 assesses the moisture content and temperature of the gas phase sample. The back-pressure regulator 154 regulates the pressure of the portion of the gas phase sample that enters the gas chromatograph 156. The portion of the gas phase sample that enters the gas chromatograph 156 is typically negligible relative to the total gas phase sample that flows through conduit 146. In certain instances, the back pressure regulator 154 alters the pressure of the portion of the gas phase that enters the gas chromatograph 156 based on pressure requirements of the gas chromatograph.

In 310, the volume of the gas phase sample is assessed by integrating output from the flow meter 144 over the sampling time. This volume may be adjusted based on chromatographic data from the gas chromatograph 156. In one example, the density or viscosity of the gas phase sample is derived from chromatographic data, and a ratio of the density or viscosity of the gas phase sample to that of the flow meter calibration gas is calculated. This ratio is used to adjust the volume of the gas sample derived from the flow meter. The adjusted volume of the gas phase sample may be sent to user interface or computing device 170 via controller 168.

In 312, the condensate-gas ratio of the hydrocarbon-containing fluid is assessed. In one example, the user interface or computing device 170 is configured to assess the ratio of the volume of the non-aqueous sample (the condensate) to the gas phase sample by dividing the volumes resulting from 308 and 310.

A number of embodiments have been described. Nevertheless, it will be understood that various modifications may be made without departing from the spirit and scope of the disclosure. Accordingly, other embodiments are within the scope of the following claims.

What is claimed is:

1. A method of analyzing a hydrocarbon-containing fluid, the method comprising:
providing a hydrocarbon-containing fluid to a cyclone separator;
separating the hydrocarbon-containing fluid into a gas phase sample and a liquid phase sample via the cyclone separator;
separating the liquid phase sample into an aqueous sample and a non-aqueous sample;
assessing the volume of the gas phase sample;
assessing the volume of the non-aqueous sample; and
assessing the condensate-gas ratio of the hydrocarbon-containing fluid, wherein the condensate-gas ratio of the hydrocarbon-containing fluid is the ratio of the volume of the non-aqueous sample to the volume of the gas phase sample.

2. The method of claim 1, wherein assessing the volume of the non-aqueous sample comprises locating an interface between the aqueous sample and the non-aqueous sample.

3. The method of claim 1, further comprising collecting the non-aqueous sample in a container after assessing the volume of the non-aqueous sample.

4. The method of claim 1, further comprising assessing the moisture content of the gas phase sample.

5. The method of claim 1, further comprising assessing the temperature of the gas phase sample.

6. The method of claim 1, wherein the hydrocarbon-containing fluid is directed from a hydrocarbon production line to an inlet of the cyclone separator.

7. The method of claim 1, wherein assessing the volume of the gas phase sample comprises adjusting the volume of the gas phase sample based on the composition of the gas.

8. The method of claim 1, further comprising assessing the composition of the gas phase sample.

9. The method of claim 8, wherein assessing the composition of the gas phase sample comprises providing a portion of the gas phase sample to a gas chromatograph.

10. The method of claim 9, where assessing the composition of the gas phase sample with the gas chromatograph comprises identifying fixed gases and C1-C5 compounds in the gas phase sample.

11. The method of claim 9, further comprising identifying an aggregate of hexanes and C6+ compounds in the gas phase sample.

12. An apparatus for analyzing a hydrocarbon-containing fluid, the apparatus comprising:
    a cyclone separator adapted to separate a hydrocarbon-containing fluid into a gas phase sample and a liquid phase sample;
    a flow meter adapted to assess a volume of the gas phase sample from the cyclone separator;
    a receptacle adapted to receive the liquid phase sample from the cyclone separator, wherein the liquid phase sample comprises an aqueous sample and a non-aqueous sample; and
    a controller operably coupled to the flow meter and the receptacle, wherein the controller is configured to assess a condensate-gas ratio of the hydrocarbon-containing fluid, and the condensate-gas ratio of the hydrocarbon-containing fluid is the ratio of the volume of the non-aqueous sample to the volume of the gas phase sample.

13. The apparatus of claim 12, further comprising a gas chromatograph adapted to receive a portion of the gas phase sample.

14. The apparatus of claim 12, further comprising a user interface communicably coupled to the controller.

15. The apparatus of claim 12, further comprising a moisture sensor and a temperature sensor communicably coupled to the controller and configured to assess the moisture and the temperature, respectively, of the gas phase sample.

16. The apparatus of claim 12, wherein the receptacle comprises a sight glass, and further comprising a camera adapted to record the location of an interface between the aqueous sample and the non-aqueous sample in the sight glass.

17. The apparatus of claim 12, wherein the cyclone separator defines a cyclone chamber having a longitudinal axis, and a length of the cyclone separator along the longitudinal axis is up to two meters.

18. The apparatus of claim 17, wherein the cyclone chamber defines a fluid inlet, a gas outlet, and a liquid outlet.

19. The apparatus of claim 18, wherein a diameter of the liquid outlet is in a range between 1 cm and 5 cm.

20. The apparatus of claim 18, wherein the cyclone chamber comprises:
    a first chamber defining the gas outlet;
    a second chamber defining the liquid outlet; and
    a third chamber between the first chamber and the second chamber defining the fluid inlet; and
    wherein the first chamber, the second chamber, and the third chamber are fluidly coupled and aligned along the longitudinal axis.

21. The apparatus of claim 20, wherein the inner diameter of the second chamber decreases linearly from the diameter of the third chamber to the diameter of the liquid outlet.

22. The apparatus of claim 20, wherein the third chamber comprises one or more trap regions, each trap region fluidly coupled to the receptacle via a conduit.

* * * * *